United States Patent [19]

Oczkowski et al.

[11] 4,354,487

[45] Oct. 19, 1982

[54] FIBER/ABSORBENT POLYMER COMPOSITES AND METHOD OF FORMING SAME

[75] Inventors: Boguslaw Oczkowski, Spotswood; Norman Schiff, Kendall Park, both of N.J.

[73] Assignee: Johnson & Johnson, New Brunswick, N.J.

[21] Appl. No.: 149,219

[22] Filed: May 12, 1980

[51] Int. Cl.³ .................. C08F 2/54; A61F 13/18
[52] U.S. Cl. .................. 128/156; 128/284; 128/290 P; 204/159.22; 427/44; 428/290
[58] Field of Search ........... 128/284, 257, 290 P, 128/290 R, 156; 427/44, 256, 289; 428/290, 291, 295, 195, 198; 204/159.22, 159.23, 159.24; 264/116, 118

[56] References Cited

U.S. PATENT DOCUMENTS

| | | | |
|---|---|---|---|
| 3,090,736 | 5/1963 | Bashaw et al. | 204/159.22 |
| 3,686,024 | 8/1972 | Narkee et al. | 428/290 |
| 3,901,236 | 8/1975 | Assarsson et al. | 128/290 R |
| 3,950,218 | 4/1976 | Levesque | 264/121 |
| 3,950,219 | 4/1976 | Levesque | 264/121 |
| 4,008,353 | 2/1977 | Gross et al. | 428/290 |
| 4,022,861 | 5/1977 | Levesque | 264/116 |
| 4,192,727 | 3/1980 | Ward | 128/290 R |
| 4,232,674 | 11/1980 | Melicon | 128/285 |

*Primary Examiner*—Michael W. Ball
*Attorney, Agent, or Firm*—Charles J. Metz

[57] ABSTRACT

There is disclosed a process which comprises:
(a) applying an aqueous solution comprising a salt of acrylic or methacrylic acid to an aggregation of fibers;
(b) irradiating said aggregation containing said aqueous solution with electromagnetic or corpuscular ionizing radiation to convert said salt of acrylic or methacrylic acid to a water-swellable polymer;
(c) individualizing the fibers to disperse the fibers and the said water-swellable polymer;
(d) collecting the individualized fibers and water-swellable polymer in the form of a fluffy batt of fibers having distributed therethrough isolated portions of water-swellable polymer affixed to individual fibers or to small groups of fibers.

17 Claims, 3 Drawing Figures

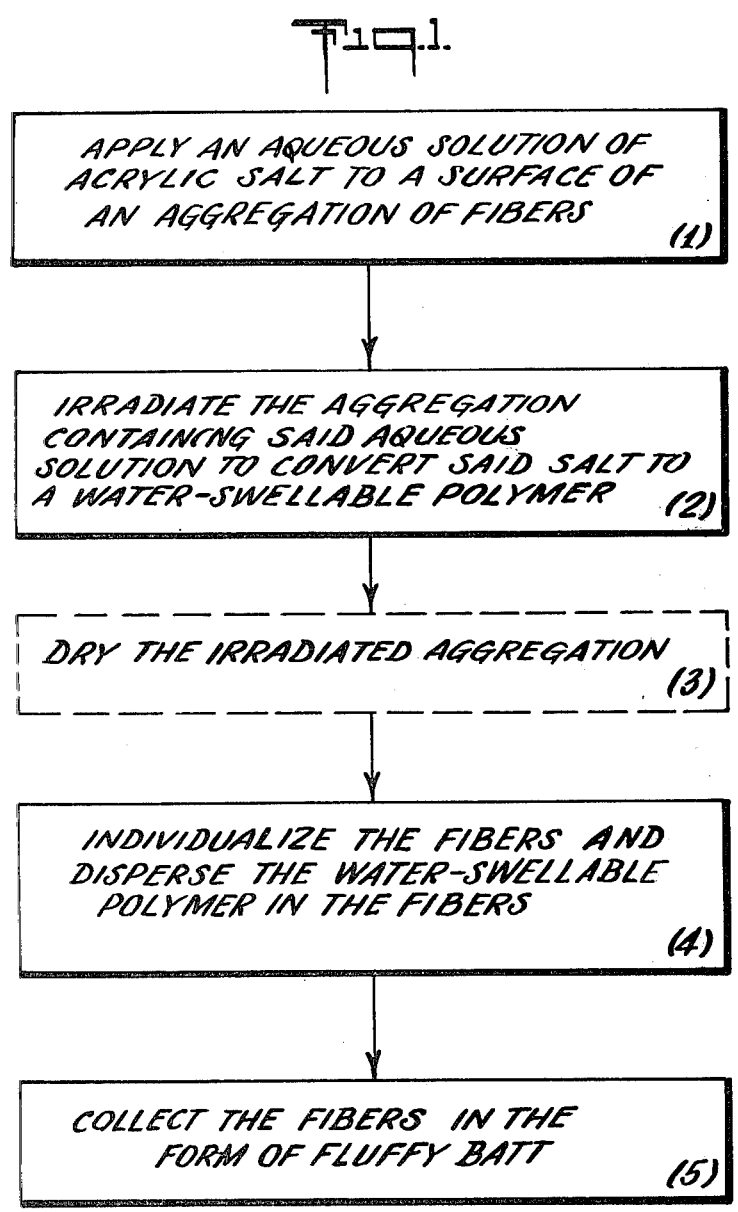

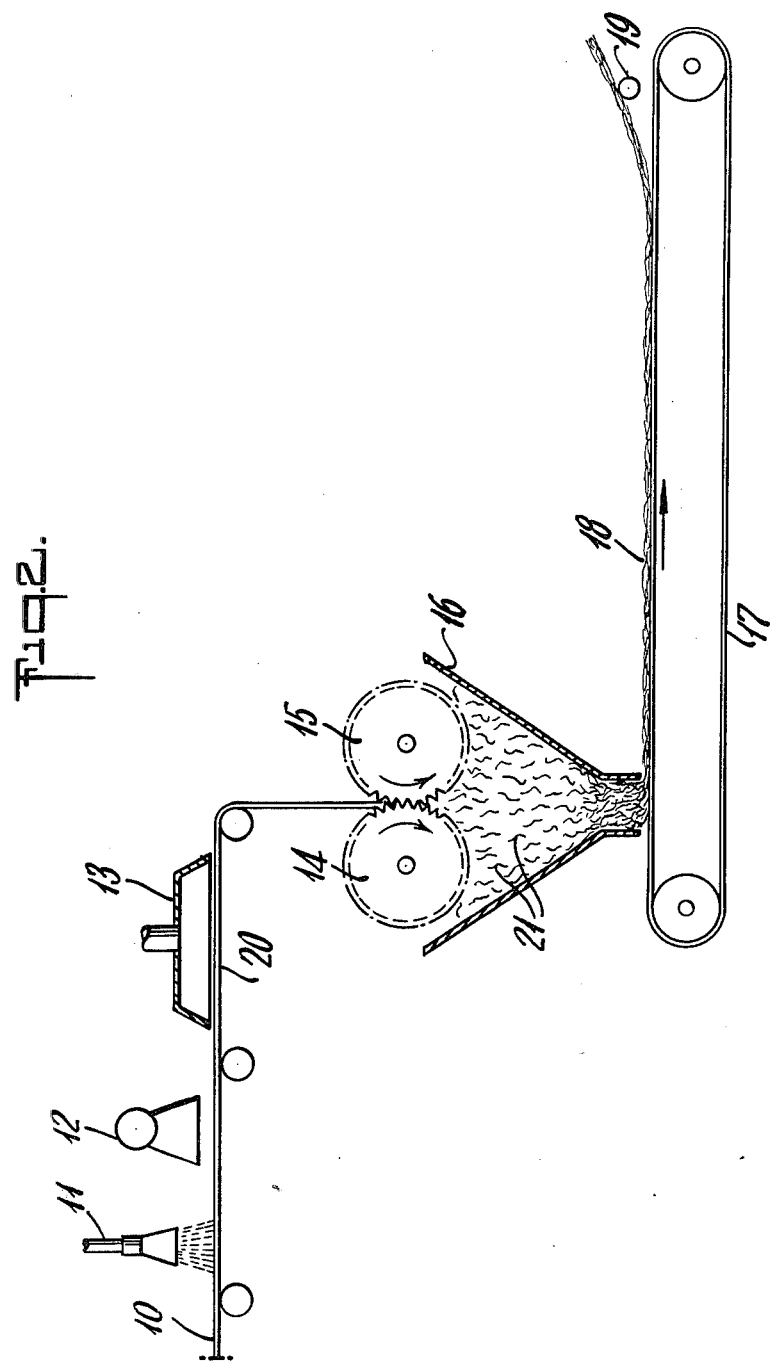

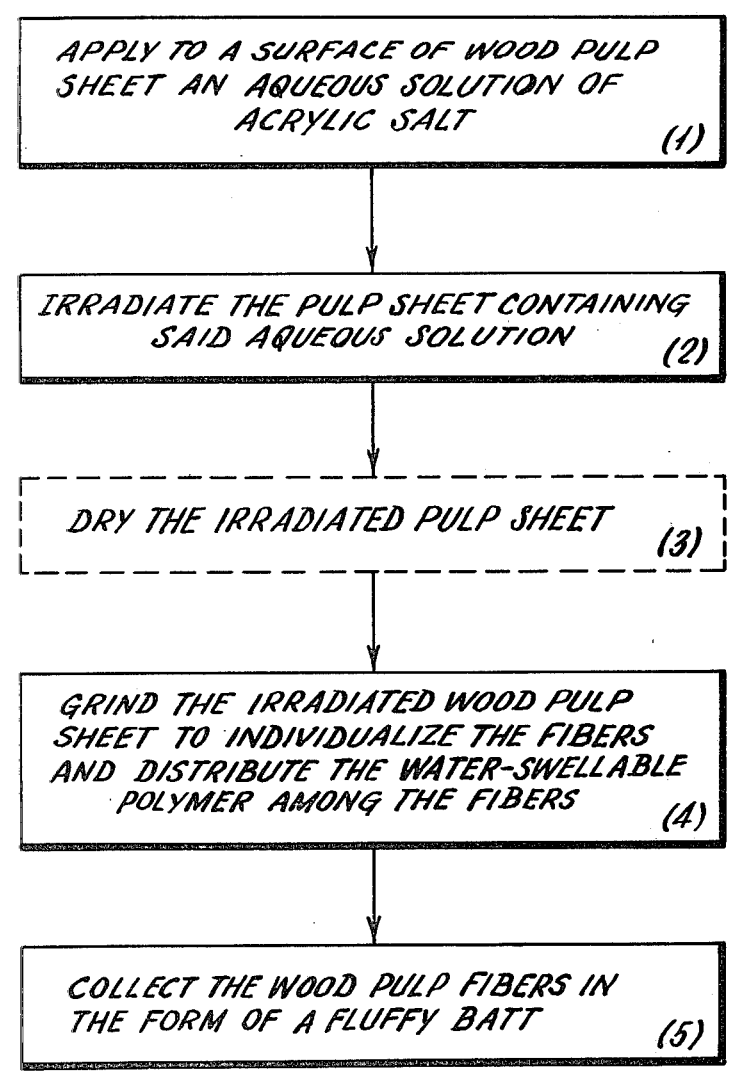

FIBER/ABSORBENT POLYMER COMPOSITES AND METHOD OF FORMING SAME

The invention relates to a method of incorporating absorbent polymers in fibrous batts in a form that facilitates the utilization of the theoretical absorbent capacity of the absorbent polymer.

BACKGROUND OF THE INVENTION

Absorbent batts made from fibers such as fluffed wood pulp fibers or other cellulosic fibers are used in sanitary napkins, disposable diapers, absorbent dressings, and other articles as a medium which is highly absorbent and has considerable capacity for holding aqueous fluids. The batts are made from individualized cellulosic fibers, usually wood pulp fibers, which are used because of their highly absorbent properties and because of their softness and low cost. However, such absorbent wood pulp or other cellulosic fiber batts have rather considerable loft or bulkiness properties, which means that the article employing such batts often tends to be rather bulky. This can add to the expense of shipping and packaging such articles. Consider, for example, the bulky packages in which disposable diapers and sanitary napkins are ordinarily marketed.

It would be a desirable objective to be able to reduce the thickness and bulkiness of wood pulp or other cellulosic fiber batts without a concomitant reduction in the liquid holding capacity of such materials. The present invention is directed to such a means whereby an absorbent polymer is incorporated in a fibrous batt, such as a wood pulp batt, in a convenient form such that it can utilize a high proportion of the theoretical capacity of the absorbent polymer. By such incorporation, the bulk or loftiness of the fibrous batt can be significantly reduced. This can reduce shipping and packaging costs, and in many such articles cases can make such articles more convenient and comfortable to wear.

It has, of course, been attempted to incorporate superabsorbent polymers into absorbent bodies for some time now. However, it is not easy to employ such superabsorbent polymers in a way that utilizes a major portion of the theoretical capacity of such polymers to absorbe liquid. The problem is that when the first portion of liquid strikes the surface of a superabsorbent polymer, a gel is formed which retards the transport of liquid therethrough and slows down and even prevents the passage of liquid to the interior of the particle of polymer. Attempts to avoid this problem by employing finely divided granules of superabsorbent polymers have met with limited success because it is difficult to affix the granules in place. Therefore, it has heretofore proven difficult to combine the obvious low cost and availability of wood pulp fibers with the high liquid holding capacity of superabsorbent polymers to produce an absorbent composite having a high capacity for holding liquid, but which has reduced bulk and loftiness when compared with wood pulp batts of similar liquid holding capacity.

Most absorbent pads, such as fluffy wood pulp batts mentioned above, have heretofore been made of all, or almost all, cellulosic fibers such as wood pulp, cotton, or rayon. The reason for this is clear—cellulosic fibers have desirable absorbent properties and are relatively inexpensive. Other types of fibers, however, have properties not possessed by cellulosic fibers, which would make them desirable to use in absorbent pads if they had absorbent properties. For instance, fusible fibers made from polyethylene or polypropylene can be heat bonded, while cellulosic fibers cannot. The ability to be heat bonded can be a significant processing advantage. The present invention provides a process for producing fluffy, absorbent fibrous batts from any kind of fiber, even from fibers which intrinsically lack absorbent properties.

BRIEF SUMMARY OF THE INVENTION

The invention provides a process for producing highly absorbent fibrous batts containing absorbent polymers in a form that is capable of achieving a relatively high proportion of the theoretical absorbent capacity of the absorbent polymer, wherein the absorbent polymer is stabilized and firmly affixed to individual fibers or small groups of fibers within the batt. The process of the invention comprises the steps of:
  (a) applying an aqueous solution comprising a salt of acrylic or methacrylic acid to an aggregation of fibers;
  (b) irradiating said aggregation containing said aqueous solution with electromagnetic or corpuscular ionizing radiation to convert said salt of acrylic or methacrylic acid to a water-swellable polymer;
  (c) individualizing the fibers to disperse the water-swellable polymer in the fibers; and
  (d) collecting the individualized fibers and water-swellable polymer in the form of a fluffy batt of fibers having distributed therethrough isolated portions of water-swellable polymer affixed to individual fibers or to small groups of fibers.

PRIOR ART

Levesque, in U.S. Pat. Nos. 3,950,218, 3,950,219, and 4,022,861, describes various procedures for making stabilized fluffly batts of wood pulp fibers by treating the surface of a fiber board with a material, grinding the treated fiber board to individualize the fibers and to distribute the material throughout the fiber, and forming a light fluffy batt of wood pulp fibers therefrom.

Assarsson et al., in U.S. Pat. No. 3,901,236, disclose the production of absorbent articles by mixing an aqueous solution of various polymers, including a copolymer of sodium acrylate and acrylamide, with cellulosic fibers, followed by subjecting the resulting mixture to ionizing radiation.

It has been disclosed to employ radiation curable polymers as the bonding agents in producing nonwoven fabrics. For instance, in U.S. Pat. No. 3,878,019 (Chapman et al.), nonwoven fabrics are produced by applying a film-forming polymer to a fibrous web substrate and subsequently cross-linking the polymer by the use of ultraviolet radiation. In U.S. Pat. No. 4,091,140 (Harmon), a radiation curable polymer in the form of a continuous filament is employed as a bonding agent in a nonwoven fabric. Similar disclosures are found in U.S. Pat. Nos. 4,146,417 (Drelich et al.), 3,709,738 (Wetherell), and 3,265,527 (Adelman).

Parker, in U.S. Pat. No. 3,770,490, discloses the production of coatings by subjecting a solution of an acrylic polymer in acrylic monomer to ionizing radiation. U.S. Pat. No. 3,090,736 (Bashaw et al.) discloses the production of insoluble, cross-linked products by subjecting aqueous soltions of salts of acrylic acid or polyacrylic acid to ionizing radiation.

Restaino, in U.S. Pat. No. 3,764,502, discloses the production of polymers of sodium acrylate by irradiating the aqueous solutions of sodium acrylate with high energy ionizing radiation. Phalangas, U.S. Pat. No. 3,948,740, and Phalangas et al., U.S. Pat. No. 4,024,040, disclose the production of water-soluble, substantially linear, high molecular weight polymers by irradiating an aqueous solution of an ethylenically unsaturated monomer and a chemical, free-radical initiator. Among the monomers disclosed are salts of acrylic and methacrylic acids.

BRIEF DESCRIPTION OF THE DRAWINGS

FIG. 1 is a flow sheet showing the various steps for carrying out the method of the invention;

FIG. 2 is a schematic view of one form of apparatus for carrying out a preferred version of the process of the invention; and FIG. 3 is a flow sheet showing the various steps in a preferred version of the process of the invention.

DETAILED DESCRIPTION OF THE INVENTION

Referring first to the drawings, in FIGS. 1 and 3 there are shown flow sheets for carrying out the broad process of the invention and one preferred version of the process of the invention. An aggregation of fibers, such as wood pulp or comminution grade which may be either a softwood pulp sheet or a hardwood pulp sheet, has applied to a surface of the aggregation a solution of a salt of acrylic or methacrylic acid in water (Box 1 of FIGS. 1 and 3).

The aqueous solution is applied to one surface, and is applied in sufficient proportion to penetrate to a predetermined depth. The treated aggregation is then irradiated with electromagnetic or corpuscular ionizing radiation, such as accelerated electrons, to convert the salt of acrylic or methacrylic acid to a water-swellable polymer (Box 2 of FIGS. 1 and 3). The fibers containing the polymerized and lightly cross-linked polymer may then be dried, if desired (Box 3 of FIGS. 1 and 3). The treated fibers are then individualized to disperse the water-swellable polymer in the fibers (Box 4 of FIG. 1). For instance, when wood pulp sheet is used, the fibers may be individualized by grinding (Box 4 of FIG. 3). The fibers containing the water-swellable polymer is then collected in the form of a lightweight batt (Box 5 of FIGS. 1 and 3).

In FIG. 2 there is schematically shown one form of apparatus that can be employed for carrying out a preferred version of the process of the invention. Pulp sheet 10 from a suitable supply is fed beneath a spray nozzle 11 to spray onto the surface of the sheet 10 the desired aqueous solution of a salt of acrylic or methacrylic acid. The sheet 10 containing the said aqueous solution is passed under an electron beam accelerator 12 and is irradiated with sufficient radiation to convert the salt of acrylic or methacrylic acid to a water-swellable polymer.

The sheet 20 with the water-swellable polymer therein may then, if desired, be passed under an oven 13 to dry the board. The sheet 20 is then fed to the nip of a pair of counterrotating toothed rolls 14 and 15, which grind and comminute the wood pulp sheet 20 and form individualized fibers 21. The sheet may be ground by any of the standard grinding mechanisms, such as counterrotating toothed rollers, Bauer mill, hammer mills, or the like.

Some of the wood pulp fibers have water-swellable polymer tightly bound or attached thereto, while other fibers are completely untreated or free of polymer. (In some cases, the polymer binds small groups of fibers together.) The fibers are dispersed in a volume of air and collected through a funnel 16 onto a moving permeable screen 17. The air passes through the screen and the fibers build up on the screen in the form of a batt 18. The batt is removed from the conveyor by a pickup roll 19 and may be wound up for further processing or may be fed directly to various converting processes.

While wood pulp fibers and other cellulosic fibers such as cotton linters and rayon are the preferred fibers for use in the invention, other types of fibers can also be used. Such other fibers include polyolefin fibers such as those made from high density polyethylene and polypropylene (which is preferably stabilized to retard radiation-induced degradation), polyester fibers, nylon fibers, modacrylic fibers, and the like. In one preferred aspect of the invention, a mixture of cellulosic fibers and heat fusible polyolefin fibers are used.

The fibers are employed in lengths of up to staple length fibers (i.e., of the order of up to 2 to 3 inches), in the form of an aggregation. Such aggregations include wood pulp sheets, random laid matts, or other types of fibrous web.

As was discussed above with respect to wood pulp sheets, one useful way to individualize the fibers and disperse the water-swellable polymer in the fibers is to grind the treated aggregation of fibers. The fiberizing can also be accomplished by use of a single-disk or double disk refiner or other equipment which subjects the sheets to alternate, rapid cycles of compression and decompression.

After individualizing, the fibers and polymer are collected in the form of a fluffy batt by known procedures, as by air laying.

An aqueous solution of a salt comprising fully or partially neutralized acrylic or methacrylic acid is employed in the invention. The salt employed can be an ammonium salt or an alkali metal salt such as a sodium or potassium salt. The degree of neutralization employed can vary in particular cases, in view of several factors. For instance, at the preferred high solution concentrations, sodium acrylate may begin to precipitate when the degree of neutralization begins to exceed about 85 percent. Therefore, it is preferred to employ sodium acrylate at about a 60 to 85 percent degree of neutralization. The more soluble ammonium and potassium acrylates, or mixed salt acrylates, can be employed at higher degrees of neutralization.

Pure methacrylate polymers do not cross-link under radiation. Therefore, methacrylate salts are used only in a mixture with acrylic salts or with a water-soluble cross-linking monomer, as explained below.

In order to reduce drying requirements in those cases wherein it is desired to dry the irradiated fibers prior to individualizing, it is preferred to employ the salt in as concentrated a solution as solubility permits. Thus, sodium acrylate is ordinarily employed in concentrations up to about 40 to 45 weight percent. The maximum concentration of other salts can easily be determined through routine experimentation.

The preferred aqueous solution for use in the invention comprises an aqueous solution of sodium acrylate.

It is permissible to include other materials in the aqueous solution. Such materials include polyfunctional, ethylenically unsaturated compounds such as methylene-bis-acrylamide, and polyethylene glycol diacrylates or dimethacrylates such as tetraethylene glycol diacrylate, as more particularly described in U.S. patent application Ser. No. 149,217,000, filed on the same day as this application by Nguyen et al. for "Cross-Linked Absorbent Polymers", and assigned to the same assignee as this application, the disclosure of which is incorporated herein by reference. These materials are employed as cross-linking agents. The polyfunctional monomer is used in small amounts, for instance, in amounts of less than one mole percent, based on moles of acrylate salt(s).

A water-soluble polymer can be employed as a viscosity adjusting agent, for example, to improve the spraying characteristics of the salt solution. Examples include polyvinyl pyrrolidone, hydroxyethyl cellulose, and similar materials.

Small amounts of polyvalent metal ions may be added to the salt to provide ionic cross-linking. Illustrations include calcium, magnesium, and aluminum.

After the aqueous solution has been applied to the aggregation of fibers, the material is then irradiated by electromagnetic or corpuscular ionizing radiation such as accelerated electrons, gamma rays, or the like, sufficient to convert the acrylic and/or methacrylic salt to a water-swellable polymer. The dose employed in particular cases will vary somewhat, depending on factors such as presence or absence of cross-linking monomers, desired degree of polymerization of the polymer, degree of cross-linking desired, and the like. In general, it is desired to irradiate the treated fibers with doses in excess of about two megarads, and preferably in excess of about three megarads. Particularly when using lower doses, it is desirable to purge oxygen from the aqueous salt solution (as by bubbling nitrogen through the solution). The maximum dose would be that dose at which degradation of the fibers begins. With cellulosic substrates, the literature reports that the dose at which degradation begins is about six megarads when gamma radiation is employed. Other forms of radiation would be expected to cause degradation at about the same dose.

After irradiating, the treated fibers may be dried to remove water by means such as forced air ovens, by infrared lamps, or the like.

The proportion of aqueous solution employed in the invention is preferably selected so that the sprayed and irradiated fibers can still be processed by standard methods to form a fluffy batt of individualized fibers. If more than a certain proportion of acrylic salt is employed, the individualized fibers may contain significant amounts of powder (as opposed to fibrous material), and it will be difficult to form a stable, fluffy batt. The exact proportion above which undesired amounts of powder are formed cannot be stated with accuracy, because it will vary with nature of materials, degree of irradiation, intended end use, etc. As a general rule, a dry add-on of about 50 weight percent or less of acrylic salt (based on weight of fibers) will enable the production of a stable, fluffy batt of fibers having both wicking and absorbency properties such that the batt is suitable for use in many absorbent applications such as sanitary napkins and disposable diapers.

EXAMPLE 1

A Georgia-Pacific comminution grade pulp sheet, marketed as "J-Flock", is impregnated with a 50 percent aqueous solution of sodium acrylate to the extent of a 10 percent dry add-on. The pulp sheet is divided into several samples, and is subjected to ½, 1, and 2 megarads, respectively, from a Dynamatron electron beam accelerator. The treated pulp sheets are then dried in an oven, are ground in Waring blenders, and assembled in the form of fluffy batts. They have enhanced absorbent properties compared with similar batts composed of the same pulp, but which do not contain the irradiated sodium acrylate material.

EXAMPLE 2

A matt of high density polyethylene staple fibers is sprayed with a 50 weight percent solution of aqueous sodium acrylate, 85 percent neutralized, to a dry add-on of 15 weight percent. The matt containing the aqueous solution is irradiated with a dose of 4 megarads by a Dynamitron electron beam accelerator. The irradiated matt is passed through a forced air oven at 110° C. for 30 seconds to partially dry the matt. The matt is then run through the nip of a pair of toothed counterrotating rolls to individualize the fibers and distribute the polymer in the fibers. The individualized fibers are then air layed to form a fluffy batt. The batt, which has excellent water absorption properties, can be heat sealed along the edges to a plastic film backing for incorporation into an absorbent product.

What is claimed is:

1. Process for producing absorbent, fluffy batts of fibers, which comprises the steps of:
   (a) applying an aqueous solution comprising a salt of acrylic or methacrylic acid to a surface of an aggregation of fibers, the amount of said solution being sufficient to penetrate said aggregation to a predetermined depth so as contact some but not all of the fibers in said aggregation, said amount being sufficient to provide not more than about 50 weight percent salt, based on weight of fibers;
   (b) irradiating said aggregation containing aqueous solution with electromagnetic or corpuscular ionizing radiation to convert said salt of acrylic or methacrylic acid to a water-swellable polymer;
   (c) individualizing the fibers to disperse the water-swellable polymer in the fibers; and
   (d) collecting the individualized fibers and water-swellable polymer in the form of a fluffy batt of fibers having distributed therethrough isolated portions of water-swellable polymer affixed to individual fibers or to small groups of fibers.

2. The process of claim 1 wherein said salt is an alkali metal salt.

3. The process of claim 2 wherein the alkali metal is sodium.

4. The process of claim 3 wherein the acid is acrylic acid.

5. The process of claim 1 wherein the aqueous solution contains a small amount of water-soluble, polyfunctional, ethylenically unsaturated compound.

6. The process of claim 5 wherein said compound is methylene-bis-acrylamide or a polyethylene glycol diacrylate or dimethacrylate.

7. The process of claim 1 wherein the aqueous solution contains a small amount of a water-soluble polymer.

8. The process of any of claims 1 through 7 wherein the electromagnetic or corpuscular ionizing radiation is accelerated electrons.

9. The process of claim 8 wherein the fibers are cellulosic.

10. The process of claim 8 wherein the aggregation of fibers is wood pulp sheet.

11. Process of any of claims 1 through 7 which includes the additional step of drying the product of step (b), prior to step (c).

12. The process of claim 9 wherein the fibers are cellulosic.

13. The process of claim 9 wherein the aggregation of fibers is wood pulp sheet.

14. The process of any of claims 1 through 7 wherein the fibers are cellulosic.

15. The process of any of claims 1 through 7 wherein the aggregation of fibers is wood pulp sheet.

16. The process of any of claim 1 through 7 wherein the fibers are fusible, thermoplastic fibers.

17. The product produced by the process of claim 1.

* * * * *

UNITED STATES PATENT AND TRADEMARK OFFICE
CERTIFICATE OF CORRECTION

PATENT NO. : 4,354,487

DATED : October 19, 1982

INVENTOR(S) : Boguslaw Oczkowski and Norman Schiff

It is certified that error appears in the above-identified patent and that said Letters Patent are hereby corrected as shown below:

Column 6 Line 32 after the word as insert "to"

Column 6 Line 36 after the word containing insert the word "said"

Signed and Sealed this

Twenty-sixth Day of June 1984

[SEAL]

Attest:

GERALD J. MOSSINGHOFF

Attesting Officer

Commissioner of Patents and Trademarks